United States Patent [19]

Swanson

[11] 4,302,855
[45] Dec. 1, 1981

[54] PLUG FOR THE INTRAMEDALLARY CANAL OF A BONE AND METHOD

[76] Inventor: Alfred B. Swanson, 2945 Bonnell, SE., Grand Rapids, Mich. 49506

[21] Appl. No.: 34,011

[22] Filed: Apr. 27, 1979

[51] Int. Cl.³ .......................... A61F 1/00; A61F 1/24
[52] U.S. Cl. ...................................... 3/1.9; 128/92 C
[58] Field of Search .................... 3/1.91, 1.911, 1.912, 3/1.913, 1.9, 1; 128/92 C, 92 CA

[56] References Cited

U.S. PATENT DOCUMENTS

| | | | |
|---|---|---|---|
| 3,008,203 | 11/1961 | Dagenhard | 249/96 |
| 3,058,225 | 10/1962 | Ward | 33/172 |
| 3,200,984 | 8/1965 | Fueslein et al. | 220/24.5 |
| 3,358,869 | 12/1967 | Palmer et al. | 220/24.5 |
| 3,738,355 | 6/1973 | Salvatore | 128/2 S |
| 3,740,779 | 6/1973 | Rubricuis | 128/303 R X |
| 3,744,061 | 7/1973 | Frost | 128/92 C X |
| 3,793,650 | 2/1974 | Ling et al. | 128/92 C X |
| 3,831,383 | 8/1974 | Crank | 166/295 X |
| 3,848,272 | 11/1974 | Noiles | 128/92 C X |
| 3,866,248 | 2/1975 | Kummer | 128/92 C |
| 3,924,274 | 12/1975 | Heimke et al. | 3/1.91 |
| 3,938,504 | 2/1976 | Dickinson et al. | 128/2 S |
| 3,943,914 | 3/1976 | Grenfell et al. | 128/2 S |
| 4,012,796 | 3/1977 | Weisman et al. | 3/1.91 |
| 4,016,867 | 4/1977 | King et al. | 128/2 S |
| 4,065,817 | 1/1978 | Branemark et al. | 3/1.91 |
| 4,245,359 | 1/1981 | Stuhmer | 3/1.9 |

FOREIGN PATENT DOCUMENTS

| | | | |
|---|---|---|---|
| 2247560 | 10/1973 | Fed. Rep. of Germany | 3/1.913 |
| 1046920 | 7/1953 | France | 128/92 C |
| 1443470 | 7/1976 | United Kingdom | 3/1.9 |

OTHER PUBLICATIONS

"Silastic Brand Intramedullary Implant (Swanson Design)"—Pamphlet by Dow Corning Corp., Medical Products Division, Midland, Mich., Jan. 1969, pp. 1-9.
"Muller Type Total Hip Prosthesis In Zimaloy", (Catalog), Cement Restrictor 4043-20; Sep. 1974.

Primary Examiner—Clifford D. Crowder
Attorney, Agent, or Firm—Price, Heneveld, Huizenga & Cooper

[57] ABSTRACT

A bone plug is disclosed for plugging the intramedullary canal of a bone to restrict the flow of cement used to affix a prosthesis. The bone plug includes a resilient body of medical grade material. The body has a smooth, blunt, rounded nose, a midportion joined to the nose and having a toroidal shape and an upper, open ended portion joined to the midportion and defining a recess. The upper, open ended portion is generally frusto-conical in shape and further defines a plurality of circumferentially spaced petal-like elements.

18 Claims, 6 Drawing Figures

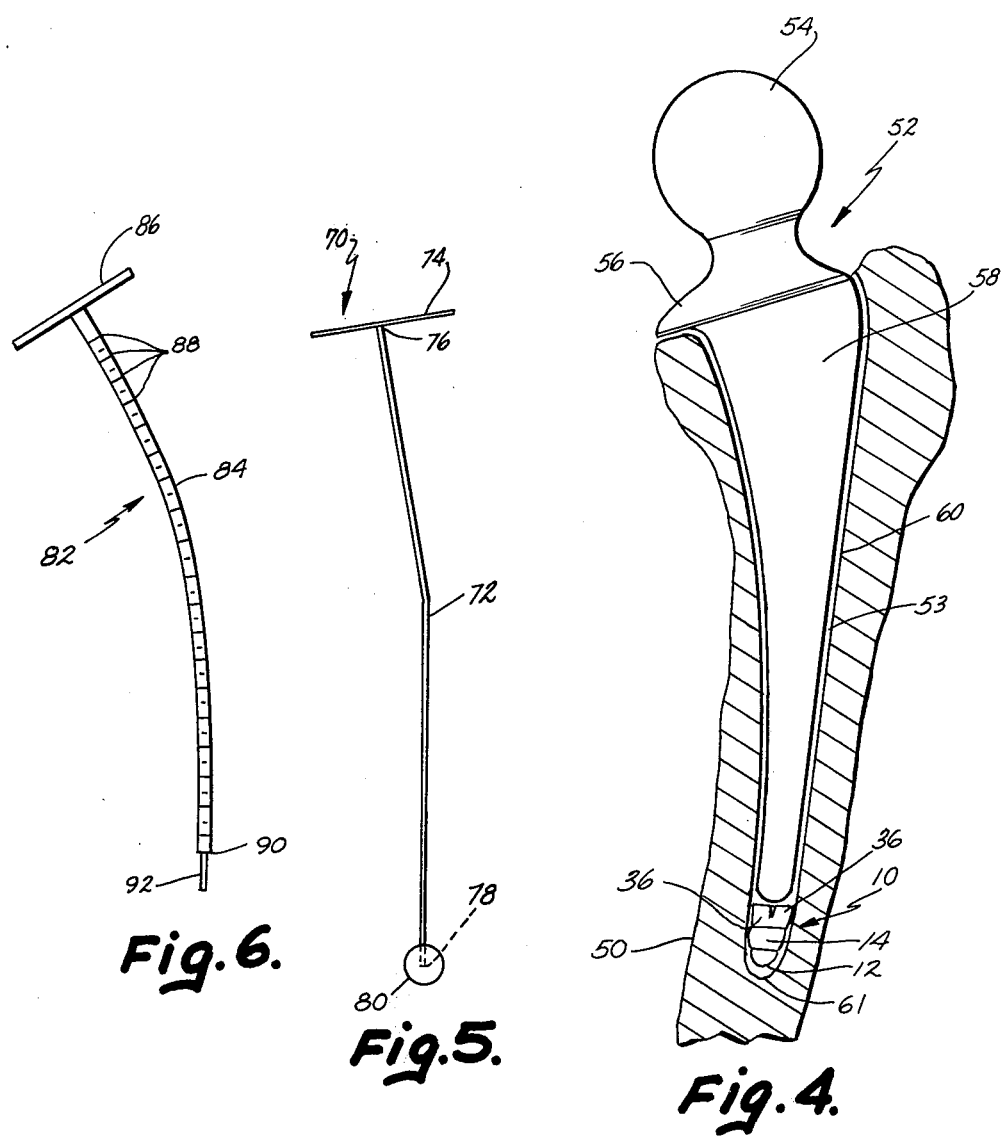

PLUG FOR THE INTRAMEDALLARY CANAL OF A BONE AND METHOD

BACKGROUND OF THE INVENTION

The present invention relates to the surgical replacement of diseased or damaged joints of the human body.

A wide variety of prosthetic devices are presently available for surgically replacing the diseased or damaged joints of the human body. Such prosthetic devices, for example, are used to replace defective finger joints, elbow joints, knee joints and hip joints. Typically, these devices include an elongated stem which is inserted into the intramedullary canal of the bone adjacent the resected joint. Some of these prostheses are fixed to an adjacent bone with a cement material.

In the total replacement of a hip joint, for example, the hip joint of the patient is exposed and the femoral head is separated from the acetabulum of the pelvis. An acetabular component is affixed to the prepared acetabulum. The femur head is surgically removed and the top of the femur and intramedullary canal are prepared for receipt of a femoral component. A cement material is inserted into the open femur canal and the stem of the femoral component is driven into the canal. The femoral component is typically fabricated from a hardened, biologically acceptable metal material such as a cobalt:chromium alloy. The stem of the prosthesis is typically fixed to the femur with a curable acrylic polymer cement such as polymethylmethacrylate. In fact, the advent of such acrylic cements for fixation of implants to the bone have made possible such newer methods for total joint replacement. Examples of such prosthetic devices may be found in U.S. Pat. No. 3,744,061, entitled ARTIFICIAL HIP JOINT AND METHOD OF IMPLANTING IN A PATIENT, issued on July 10, 1973 to Frost; U.S. Pat. No. 3,793,650, entitled PROSTHETIC BONE JOINT HAVING A SPACER DEVICE, issued on Feb. 26, 1974 to Ling et al; and U.S. Pat. No. 3,866,248, entitled CEMENT RESTRICTOR FOR TOTAL HIP OPERATION, issued on Feb. 18, 1975 to Kummer.

Various problems have been experienced with employment of a bone cement for fixation of the stem of a prosthesis to the bone. Some of these problems are particularly acute with respect to affixation to long bones such as the femur during total hip replacement. These problems are primarily related to limitation of the cement to the area of the stem of the prosthesis within the open canal of the bone. The cement may travel beyond the area of affixation in a long bone. Proper fixation of the prosthesis to the bone may not be accomplished without taking steps to limit the travel of the cement.

An approach which has heretofore been taken to prevent or alleviate the problem of cement travel involves the injection of a quantity of cement within the bone at the lowest point of affixation. The cement is allowed to cure in order to form a plug or bolus of cement prior to insertion of the rest of the cement used for fixing the stem of the implant to the bone. This method may not be fully acceptable due to the delay necessitated for proper curing of the cement plug, problems related to the adequacy of the seal formed by the plug and problems with insertion of an adequate quantity of cement at the correct location. Also, the cement plug may travel down the bone prior to curing or it may be extruded out of the bone.

SUMMARY OF THE INVENTION

In accordance with the present invention, a unique article and method are provided whereby the problems heretofore experienced with the use of a cement to affix a prosthetic device to a bone are substantially eliminated. Essentially, the article comprises a bone plug defined by a resilient body of medical grade material. The body is generally frusto-conical in shape and has a recess opening through an upper end thereof. The body is deformable when inserted into the canal and effects a seal with the bone surface.

The plug prevents the travel of cement beyond the point of affixation, permits the cement to be forced into the bone under pressure to insure flow of the cement into the interstices of the bone, and due to its configuration, migration or extrusion of the plug back out of the canal is prevented. The plug also assists in positioning the prosthesis stem within the canal.

The method contemplated by the present invention includes the steps of preparing the canal of the bone for receipt of the stem of a prosthesis and inserting a resilient body into the canal a distance approximately equal to the length of the stem.

BRIEF DESCRIPTION OF THE DRAWINGS

FIG. 4 is a sectional view of a femur bone illustrating affixation of the stem of a femoral prosthesis component within the bone using a plug in accordance with the present invention;

FIG. 5 is an elevational view of an instrument useable to select the proper plug size; and FIG. 6 is an elevational view of an instrument useable to position or insert the plug within a bone.

DETAILED DESCRIPTION OF THE PREFERRED EMBODIMENT

Figure 2:
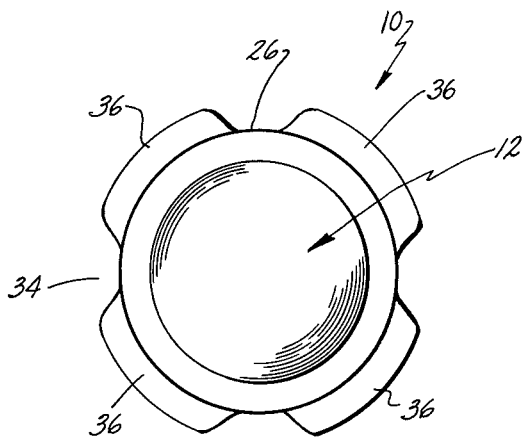
FIG. 2 is an end, plan view thereof.
Figure 1:
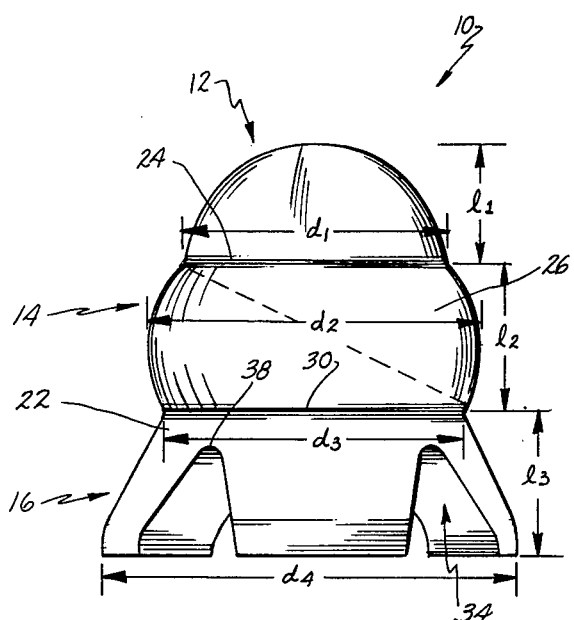
FIG. 1 is an elevational view of a bone plug in accordance with the present invention.
Figure 3:
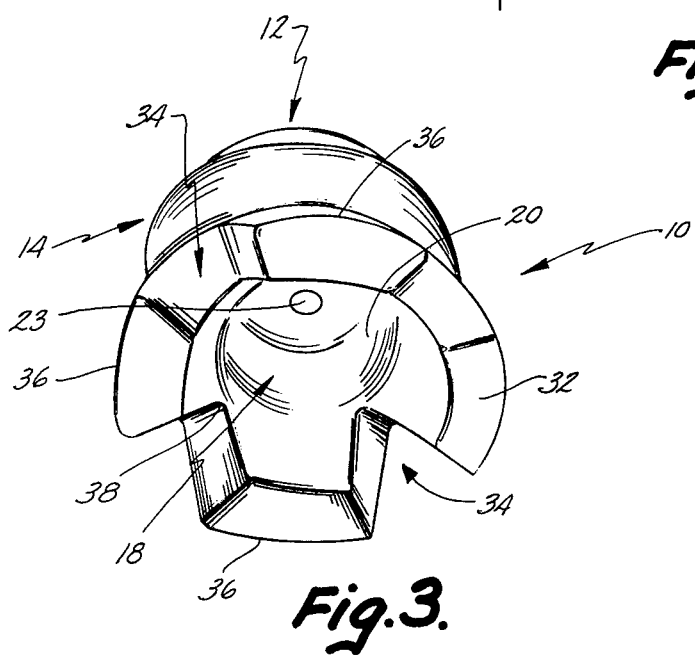
FIG. 3 is a perspective view thereof.

The preferred embodiment of a bone plug or article for plugging the intramedullary canal of a bone is illustrated in FIGS. 1–3 and generally designated 10. As shown therein, the plug 10 is fabricated as a one-piece body having a generally frusto-conical shape. In the preferred form, the plug includes an inferior or lower end or nose 12, a midportion 14 and a superior or upper end portion 16. As seen in FIG. 3, the body of the plug 10 defines an open recess or cup-like area generally designated 18. The recess includes a bottom 20 which may be smoothly rounded or flat. Recess 18 is bounded by a wall 22 which defines superior end portion 16. In the preferred form for reasons explained below, bottom 20 includes an opening or bore 23 centrally positioned and opening therethrough.

As seen in FIG. 2, inferior end or nose 12 of the body is smoothly rounded, semi-circular and blunt in shape. The midportion 14 is joined at a boundary line 24 to nose 12. Midportion 14 is generally toroidal in shape and therefore defines a smoothly rounded protuberance which extends circumferentially around the entire midportion of the body of the plug 10. The surface 26 of the midportion 14, as explained below, performs the primary sealing function of plug 10. Superior end portion 16 defined by wall 22 is joined to midportion 14 along a line 30 which extends circumferentially around the entire plug 10.

In the preferred construction, wall 22 is generally frusto-conical in shape and tapers outwardly from line 30 towards an end surface 32 of wall 22. Wall 22 includes a plurality of equally spaced, generally V-shaped notches 34. In the preferred construction, four circumferentially spaced notches 34 are provided in wall 22. The notches define with wall 22 a plurality of circumferentially spaced petal-like elements 36. As seen in FIG. 3, bottom wall 20 of recess 18 is positioned below the apex 38 of each of the notches 34. Recess 18, therefore, extends below the petals.

Plug 10 is fabricated as a single piece from a resilient, medically acceptable material. It is presently preferred that the material be a medical grade silicone polymer rubber. Such materials are presently sold by Dow Corning Corporation under the trademark Silastic.

The configuration of the plug 10 and the resiliency of the plug results in an effective seal between the plug and the inner surface of a bone within the intramedullary canal. This seal prevents travel of acrylic cement or other bone cements past the plug within the open canal thereby limiting the cement to the area of the stem of a prosthesis.

Due to the configuration of the preferred embodiment of the present invention, extrusion or migration of the plug back out of the canal is prevented. In the preferred construction, petal elements 36 and notches 34 are configured so that they may be moved towards each other. When side surfaces 42, 44 of the notches contact, the petals define a recess having a generally rectangular shape in section. The natural resiliency of the material from which the plug is fabricated biases the petal elements outwardly into engagement with the inner bone surface.

In a presently existing embodiment of a bone plug in accordance with the present invention, the overall length $l_1$ of the nose 12 is approximately 0.215 inches. The overall length $l_2$ of the midportion 14 is approximately 0.375 inches and the overall length of $l_3$ of portion 16 is approximately 0.30 inches giving a total overall length of approximately 0.89 inches. The maximum diameter $d_1$ of the semi-spherical shaped nose portion 12 is approximately 0.43 inches. The maximum diameter $d_2$ of the midportion 14 is approximately 0.70 inches. The diameter of circumferential line 30 is approximately 0.62 inches and the maximum diameter $d_4$ of portion 16 is approximately 0.80 inches. Four petal-like elements 36 are provided and the plug is symmetrical about a vertical centerline.

Use of plug 10 in the affixation of a femoral component 52 to a femur bone 50 having an intramedullary canal 60 with a cement 53 is illustrated in FIG. 4. Component 52, as illustrated, includes a head or ball portion 54, a stop or collar 56 and an elongated, tapered stem 58. The femur bone has had the head portion thereof surgically removed and intramedullary canal 60 prepared for receipt of stem portion 58. Bone plug 10 in accordance with the present invention is inserted within open intramedullary canal 60 to a predetermined depth corresponding to the depth of insertion of stem 58. Preferably, plug 10 is positioned 1 to 1½ cms. distally of the lower end of stem 58. Cement 53 will therefore, surround the implant. This results in more even force distribution and better affixation. The generally frusto-conical shape of plug 10 increases the ease with which the plug may be pushed into the intramedullary canal.

When forced into canal 60, plug 10 will deform and the midportion 14 forms an effective seal with surface 61 of the intramedullary canal 60. Petals 36 move towards each other thereby partially closing or fully closing the notches 34. The configuration of petals 36 and their angular relationship with the midportion 14 and nose 12 prevents extrusion of the plug back out of the open canal 60. Portions of end surface 32 of wall 22 will be biased into engagement with surface 61 of the canal 60. The resilience of the body biasing the petals serves to effectively retain the plug in position.

Plug 10 must be provided in a plurality of graduated sizes in order to insure a proper fit, match or seal between the plug and the particular bone size encountered. FIG. 5 illustrates an instrument generally designated 70 for determining the proper size of plug to be used. Instrument 70 preferably includes an elongated length of resilient wire 72 which may be slightly bent or curved along an upper portion to conform more closely to canal 60. A handle 74 is secured to an upper end 76 of wire 72 or formed integral therewith. Lower end 78 of wire 72 has removably secured thereto a bulb or ball 80 of spherical shape. A plurality of bulbs 80 are provided in graduated sizes corresponding to the graduated sizes of the bone plugs. Each bulb 80 includes a bore and the bulb is pressed onto end 78 of instrument 70. Bulbs 80 may be fabricated from silicone rubber. In use, a size is selected, fixed to end 78 and pushed into the canal as far as possible. The distance of insertion is compared to the length of the prosthesis stem. Different size bulbs are inserted until the proper size is found. The correct plug size is readily determined from the final bulb size used, since the bulbs correspond to plug sizes.

An instrument generally designated 82 in FIG. 6 is provided to insert the proper size bone plug to the correct depth within the canal. Instrument 82 is a rod-like device including a portion 84 having a handle 86 affixed thereto. Portion 84 is a cylindrical, metal rod approximately ¼ inch in diameter. The upper length of portion 84 is preferably curved to approximately the curvature of canal 60. Also, portion 84 has formed thereon graduated calibration marks 88. Marks 88 are equally spaced along the length of portion 84 and measure the depth of insertion within the canal. Given the overall length of stem 58, instrument 82 permits the plug to be positioned 1 to 1½ cms. below the stem when implanted within the bone. Affixed to a lower end 90 or formed integral therewith is a reduced diameter, blunt spike-like element 92. Element 92 is dimensioned to be snugly received within bore 23 formed in and opening through wall 20 of plug 10. Element 92, therefore, secures plug 10 to the insertion instrument 82. In use, a plug 10 is pressed onto element 92 and the instrument is used to push the plug into canal 60.

Once plug 10 is pushed into the intrameduallary canal, acrylic cement is forced into the open end of the canal. Suction tubes are preferably employed to draw out air within the canal as the cement is put in. The cement is inserted and pushed in under pressure with the fingers of the surgeon. This pushing under pressure forces the cement into the bone interstices. The plug defines an effective seal with the intrameduallary canal, prevents the cement from traveling beyond the desired point of fixation and allows the cement to be applied under pressure. This results in better acrylic cement affixation of the stem to the bone.

Once the cement is forced into position, the implant stem is then forced into the open intramedullary canal.

As the implant is forced into the canal, cement will extrude upwardly out of the open canal and the same will be removed. The recessed or hollowed out portion of plug 10 permits the plug body and the petals 36 to collapse for insertion providing the effective seal.

In view of the above description, it should now be readily apparent to those of ordinary skill in the art that the present invention substantially alleviates the problems heretofore experienced with the use of cement to affix the stem of a prosthesis within a bone canal. It is believed that various modifications to the preferred embodiment of the invention as illustrated and described could be made without departing from the inventive concepts disclosed herein. For example, the specific configuration of the plug could be varied somewhat from that illustrated as long as the generally frusto-conical shape is retained and a recess is provided to permit collapse of the plug within the canal. The overall shape increases ease of insertion, insures an adequate seal and prevents extrusion outwardly of the plug from the canal. Although described and shown in the context of a total hip joint replacement, the present invention may be used in the fixation of any prosthesis using a cement.

Therefore, it is expressly intended that the above description should be considered as that of the preferred embodiment. The true spirit and scope of the present invention may be determined by reference to the appended claims.

The embodiments of the invention in which an exclusive property or privilege is claimed are defined as follows:

1. An article for plugging an open ended intramedullary canal of a bone to restrict the flow of a cement used to fix a prosthesis inserted into the open end of the canal, said article comprising:
    a resilient body of medical grade material, said body being generally frusto-conical in shape and having a lower end and an upper end, said body tapering inwardly from said upper end to said lower end, said upper end including a wall defining a recess opening through the upper end of the body, said body upper end being deformable within an intramedullary canal to seal the canal, prevent extrusion of the article back out of the open canal and prevent flow of cement therebeyond.

2. An article as defined by claim 1 wherein said body lower end includes a rounded, convexly shaped nose and said recess includes a bottom having a centrally positioned bore opening therethrough whereby an insertion instrument may be disposed within said bore and said article may be inserted into said canal.

3. An article for plugging the intramedullary canal of a bone to restrict the flow of a cement used to fix a prosthesis, said article comprising:
    a resilient body of medical grade material, said body being generally frusto-conical in shape and defining a recess opening through the upper end of the body, said body being deformable within an intramedullary canal to seal the canal and prevent flow of cement therebeyond, said body including a smoothly rounded toroidal shaped protuberance extending circumferentially around a midportion of the body.

4. An article for plugging the intramedullary canal of a bone to restrict the flow of a cement used to fix a prosthesis, said article comprising:
    a resilient body of medical grade material, said body being generally frusto-conical in shape and defining a recess opening through the upper end of the body, said body being deformable within an intramedullary canal to seal the canal and prevent flow of cement therebeyond, an upper portion of said body including a plurality of circumferentially spaced, flexible petals, said body having notches separating said petals and said recess extending below each of said petals whereby the petals will move towards each other, closing off the notches as the body is deformed within an intramedullary canal.

5. An article for plugging the intramedullary canal of a bone to restrict the flow of a cement used to fix a prosthesis, said article comprising:
    a resilient body of medical grade material, said body being generally frusto-conical in shape and defining a recess opening through the upper end of the body, said body being deformable within an intramedullary canal to seal the canal and prevent flow of cement therebeyond, said body including a rounded, convexly shaped nose, and said body including a smoothly rounded toroidal shaped protuberance extending circumferentially around a midportion of the body.

6. An article as defined by claim 5 wherein an upper portion of said body includes a plurality of circumferentially spaced, flexible petals, said body having notches separating said petals and said recess extending below each of said petals whereby the petals will move towards each other, closing off the notches as the body is deformed within an intramedullary canal.

7. An article for plugging the intramedullary canal of a bone to restrict the flow of a cement used to fix a prosthesis, said article comprising:
    a resilient body of medical grade material, said body being generally frusto-conical in shape and defining a recess opening through the upper end of the body, said body being deformable within an intramedullary canal to seal the canal and prevent flow of cement therebeyond, said body including a rounded, convexly shaped nose, and an upper portion of said body including a plurality of circumferentially spaced, flexible petals, said body having notches separating said petals and said recess extending below each of said petals whereby the petals will move towards each other, closing off the notches as the body is deformed within an intramedullary canal.

8. A bone plug fabricated as a one-piece member from a resilient material, said bone plug comprising:
    a nose having a smooth, blunt, rounded shape;
    a midportion joined to said nose and having a toroidal shape, said midportion serving as a seal; and
    an upper, open ended portion joined to said midportion and defining a recess.

9. A bone plug as defined by claim 8 wherein said upper open ended portion is generally frusto-conical in shape and includes a wall defining said recess.

10. A bone plug as defined by claim 9 wherein said wall defines a plurality of generally V-shaped notches opening therethrough so that said wall defines a plurality of circumferentially spaced petal-like elements.

11. A bone plug as defined by claim 10 wherein the maximum diameter of said midportion is greater than the maximum diameter of said nose and less than the maximum diameter of said wall.

12. A method of replacing a diseased or damaged joint with a prosthetic device of the type including a stem fixable within the intramedullary canal of an open ended bone adjacent the joint, said method comprising the steps of:

preparing the canal of the bone for receipt of the stem of a prosthesis;

inserting a plug into the canal a distance approximately equal to the length of the stem, said plug comprising a tapered resilient body of medical grade material, said body having a lower end and an upper end including a wall defining a recess opening through the top of said body, said body tapering inwardly from said upper end to said lower end and said body deforming within the canal to define a seal with the canal, said body being inserted into the canal lower end first;

inserting a cement material into the canal and forcing the cement material into bone interstices, said plug preventing the cement material from flowing beyond the plug; and inserting the stem of the prosthesis into the canal.

13. A method as defined by claim 12 further including the step of drawing out air from the canal while inserting the cement material into the canal.

14. A method as defined by claim 13 wherein said body is generally frusto-conical in shape and said lower end includes a rounded, convexly shaped nose.

15. A method as defined by claim 14 wherein said body further includes a smoothly rounded toroidal shaped protuberance extending circumferentially around a midportion of the body.

16. A method as defined by claim 15 wherein said wall of said upper end of said body defines a plurality of circumferentially spaced, flexible petals, said petals dimensioned and positioned so as to close towards one another as the plug is deformed within the canal.

17. A method as defined by claim 12 further including the steps of:

providing a sizing instrument having an elongated portion capable of carrying a bulb on one end;

providing a plurality of different size bulbs calibrated to different sizes of plugs;

inserting the instrument carrying one of the bulbs into the intramedullary canal as far as it will go; and comparing the depth of insertion to the length of the prosthesis stem and if the depth of insertion corresponds to the length of the stem, selecting a plug based upon the size of bulb used.

18. A method of replacing a diseased or damaged joint with a prosthetic device of the type including a stem fixable within the intramedullary canal of a bone adjacent the joint, said method comprising the steps of:

preparing the canal of the bone for receipt of the stem of a prosthesis;

inserting a plug into the canal a distance approximately equal to the length of the stem, said plug comprising a resilient body of medical grade material, said body defining a recess opening through the top thereof and said body deforming within the canal to define a seal with the canal;

inserting a cement material into the canal and forcing the cement material into bone interstices, said plug preventing the cement material from flowing beyond the plug;

inserting the stem of the prosthesis into the canal;

providing a sizing instrument having an elongated portion capable of carrying a bulb on one end;

providing a plurality of different size bulbs calibrated to different sizes of plugs;

inserting the instrument carrying one of the bulbs into the intramedullary canal as far as it will go; and comparing the depth of insertion to the length of the prosthesis stem and if the depth of insertion corresponds to the length of the stem, selecting a plug based upon the size of bulb used, and wherein the step of inserting a plug further includes the steps of:

providing an elongated, rod-like insertion instrument;

pressing a plug onto the lower end of the insertion instrument; and inserting the instrument into the canal and pushing the plug into position, said insertion instrument having calibrated markings thereon so that the depth of insertion may be determined.

* * * * *